US006379719B1

(12) United States Patent
Gilles

(10) Patent No.: US 6,379,719 B1
(45) Date of Patent: Apr. 30, 2002

(54) **USE OF AT LEAST ONE PROTEIN FRACTION EXTRACTED FROM *HIBISCUS ESCULENTUS* SEEDS AND COSMETIC COMPOSITION CONTAINING SUCH A FRACTION**

(75) Inventor: Pauly Gilles, Nancy (FR)

(73) Assignee: Laboratories Serobiologiques (Societe Anonyme), Pulnoy (FR)

( * ) Notice: Subject to any disclaimer, the term of this patent is extended or adjusted under 35 U.S.C. 154(b) by 0 days.

(21) Appl. No.: 09/713,209

(22) Filed: Nov. 16, 2000

Related U.S. Application Data

(63) Continuation of application No. 09/403,256, filed as application No. PCT/FR98/00715 on Apr. 8, 1998.

(51) Int. Cl.$^7$ .......................... A61K 6/00; A61K 35/78; A01N 65/00
(52) U.S. Cl. ........................ 424/776; 424/401; 424/725
(58) Field of Search .............................. 424/195.1, 725, 424/776

(56) References Cited

U.S. PATENT DOCUMENTS 4,018,755 A    4/1977   Wang

FOREIGN PATENT DOCUMENTS

FR    2 679 443    1/1993
JP    58088305     5/1983

OTHER PUBLICATIONS

L.A. Bryant et al., "Processing, Functional, and Nutritional Properties of Okra Seed Products", Journal of Food Science, vol. 53, No. 3, 1998, pp. 810–816.

F. Ogata et al., "Purification and Characterization of Four Trypsin Inhibitors from Seeds of Okra, *Abelmoschus esculentus* L.", Argic. Biol. Chem., vol. 50, No. 9, pp. 2325–2333.

F. Martin et al., "Protein, Oil and Gossypol Contents of a Vegetable Curd Made from Okra Seeds", Journal of Food Science, vol. 44, 1979, pp. 1517–1529.

*Primary Examiner*—Jon P. Weber
*Assistant Examiner*—Patricia Patten
(74) *Attorney, Agent, or Firm*—Young & Thompson

(57) ABSTRACT

The present invention relates to a use of at least one protein fraction extracted from *Hibiscus esculentus* seeds and to a cosmetic composition containing such a fraction. Use of at least one soluble protein fraction extracted from *Hibiscus esculentus* seeds or okra as a substitute for casein in a cosmetic composition or product, the composition containing between 0.01% and 50.00% of the fraction.

5 Claims, 6 Drawing Sheets

Figure 1:
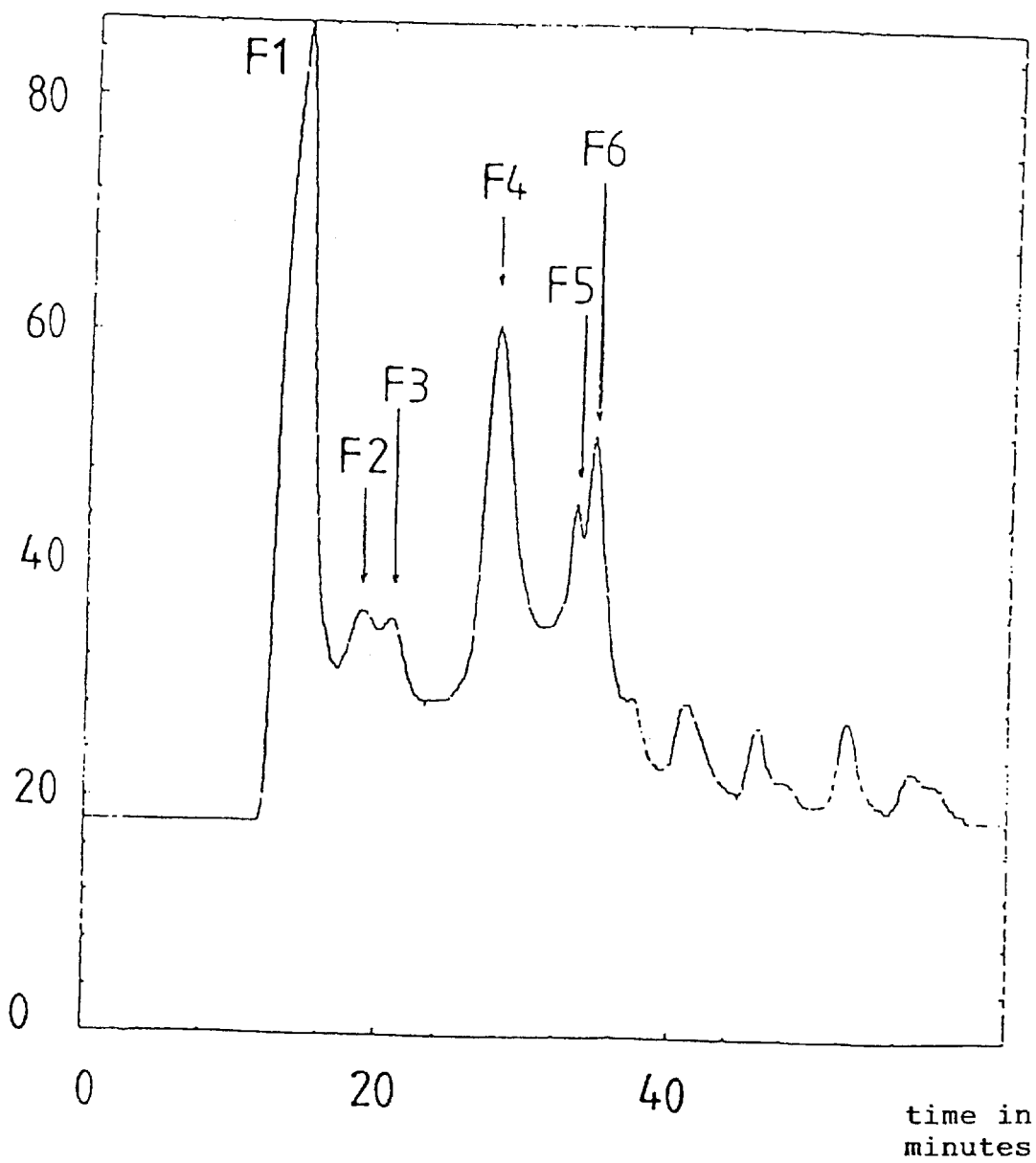

USE OF AT LEAST ONE PROTEIN FRACTION EXTRACTED FROM *HIBISCUS ESCULENTUS* SEEDS AND COSMETIC COMPOSITION CONTAINING SUCH A FRACTION

CROSS-REFERENCE TO RELATED APPLICATIONS

This application is a continuation of copending application Ser. No. 09/403,256, filed Oct. 18, 1999, which was the 35 USC 371 national phase of International application PCT/FR98/00715 filed on Apr. 8, 1998, which designated the United States.

FIELD OF THE INVENTION

The present invention concerns the field of cosmetology, in particular cutaneous and capillary applications, and relates to the use of at least one protein fraction extracted from *Hibiscus esculentus* and to a composition containing at least one such extract.

BACKGROUND OF THE INVENTION

The *Hibiscus esculentus* (Abelmoshus esculentus or Okra from the Malvaceae family) is a plant of African origin introduced into the United States and East Indies under the Spanish name of gumbo. It is one of the botanical species which has been cultivated for its pods for more than 2,000 years.

Okra grows in numerous regions of the world such as India, Malaysia, the Philippines, America (Mid-West), Mediterranean regions, Africa and, more generally, in tropical regions.

The fruits (pods) which are eaten young as vegetables are long, green and tapering; they have a delicate flavour and a mucilaginous internal texture.

Apart from the pods, which are of interest on account of the gum which they contain, research has also been carried out on the seeds of *Hibiscus esculentus* in order to study their potential as a new source of proteins.

To this end, the chemical composition of the whole seed of different varieties of okra (outer skin plus endosperm) has been determined.

Similarly, the properties (protein solubility, amino acid composition, emulsification capacity, foaming capacity, nutritional value) of various products obtained from the seeds (whole flour prepared from skinned seeds, delipidated flour, concentrate and protein isolate) have been studied for food purposes (see, for example, Bryant L A, Montecalvo J, Morey K S, Loy B: "Processing, functional and nutritional properties of okra seed products", Journal of food science, vol. 53, No. 3, 818–816).

Okra seed mainly contains the following substances in % by weight, relative to the dry material:

17.7 to 21.8% of proteins
14.7 to 20.06% of lipids
4.33 to 4.62% of ash
6.84 to 7.92% of water
0.0032% of gossypol, and, in particular, traces of the following substances:

| | |
|---|---|
| Calcium: | 282.26 mg/100 g |
| Iron: | 10.26 mg/100 g |
| Thiamine: | 0.69 mg/100 g |
| Riboflavin: | 0.14 mg/100 g |
| Niacin: | 4.01 mg/100 g |
| α-tocopherol: | 30.4 mg/100 g. |

(See Karakoltsidis P A, Constantidines S M: "okra seed: a new protein source", J. Agric Food Chem., 1975, 23 No. 6, 1204–1207/Wandawi A L: "Chemical composition of seeds of two okra cultivars *Abelmoschus esculentus*", Journal of agricultural and food chemistry, 1983, 31 No. 6, 1355–1358).

The amino acid composition of concentrated *Hibiscus esculentus* seed proteins or protein isolates resembles that of soya proteins and is close to that of casein (see table below).

| Amino acid g/16 g of nitrogen | Hibiscus (seeds) Karakoltsidis et al Mandawi AL | Hibiscus (seeds) Bryant et al | Protein concentrate Bryant LA et al | Protein isolate Bryant LA et al | Soya (seed) Karakoltsidis et al | Casein Karakotsidis et al |
|---|---|---|---|---|---|---|
| Asp | 11.82 to 15.47 | 11.57 | 10.89 | 12.12 | 17.00 | 7.11 |
| Thr | 3.02 to 4.38 | 2.86 | 3.37 | 2.90 | 5.47 | 4.65 |
| Ser | 5.25 to 6.71 | 5.07 | 5.23 | 4.97 | 7.42 | 6.02 |
| Glu | 20.48 to 22.08 | 15.91 | 19.15 | 17.35 | 21.05 | 21.19 |
| Pro | 3.83 to 6.06 | 3.79 | 4.88 | 4.98 | 7.71 | 11.54 |
| Gly | 5.79 to 6.66 | 4.78 | 7.77 | 4.16 | 4.32 | 1.97 |
| Ala | 5.89 to 6.66 | 4.83 | 4.53 | 4.59 | 6.13 | 3.07 |
| Val | 4.0 to 6.4 | 4.24 | 4.42 | 4.33 | 5.26 | 6.72 |
| Cys | 1.54 to 2.53 | 3.63 | 1.89 | 1.90 | 1.61 | 0.36 |
| Met | 1.29 to 1.85 | 1.83 | 2.18 | 2.21 | 1.25 | 2.78 |
| Ile | 3.15 to 4.65 | 2.96 | 3.06 | 3.13 | 4.46 | 5.40 |
| Leu | 6.68 to 8.47 | 6.21 | 6.96 | 6.97 | 9.35 | 9.49 |
| Tyr | 3.6 to 3.83 | 3.46 | 5.15 | 4.03 | 3.72 | 5.81 |
| Phe | 3.93 to 4.7 | 4.41 | 4.80 | 4.85 | 5.26 | 5.23 |
| Lys | 7.24 to 8.9 | 6.22 | 6.19 | 6.47 | 8.00 | 8.80 |
| His | 1.78 to 2.99 | 2.34 | 3.61 | 3.83 | 2.67 | 2.91 |
| Arg | 11.04 to 12.46 | 11.17 | 10.02 | 9.98 | 10.07 | 3.74 |
| Trp | 0.85 to 0.96 | 2.02 | 2.57 | 2.03 | nd | nd |

With regard to the casein, close contents of threonine, serine, glutamic acid, valine, isoleucine, leucine, phenylalanine, lysine and histidine are noted in particular.

The various aforementioned studies therefore demonstrate the value of *Hibiscus esculentus* seeds as potential sources of proteins from a food point of view.

Furthermore, the use for dermatological purposes of a viscous liquid product obtained by hot extraction and/or extraction under pressure from the fruits of *Hibiscus esculentus* (FR-A-2 679 443) as well as the use of a powdered material composed of polysaccharide extracted from immature *Hibiscus esculentus* seeds in a cosmetic product (JP-A-57/199969) are also known.

SUMMARY OF THE INVENTION

Now the inventors have found that it was possible to use extracts of *Hibiscus esculentus* seeds directly in cosmetics and that the use of at least one preferably soluble protein fraction extracted from *Hibiscus esculentus* or okra seeds, in particular as a substitute for casein, in a cosmetic composition or product yielded a composition or product having surprising and advantageous specific properties.

A strong cellular nutritive power, a smoothing and biofilm-forming effect, conditioning, restructuring and repairing effects as well as anti-irritant, light-protecting, soothing and cutaneous anti-ageing effects have thus been found.

The aforementioned extracts can be used not only for skin care and hygiene applications (products for the face or for the body, day or night products, solar products, anti-wrinkle hygiene products, slimming products), but also in the field of hair care and hygiene (lotions or shampoos; creams; mousses; protective products, repairing products, softeners, film-forming agents and light protectors; perming and colouring products).

Proteins can be prepared by conventional methods of extraction of vegetable proteins and preparation of protein concentrates or isolates known to a person skilled in the art and described, in particular, in the aforementioned article by Bryant L A, Montecalvo J, Morey K S and Loy B.

The raw material consists of *Hibiscus esculentus* seeds or seed flour (protein content=21.6 relative to the dry material).

The flour thus obtained may be delipidated by extraction in hexane at 45° C. (advantageously 3 successive extractions).

The oil yield is 16.2 to 23.9% by weight, depending on whether the starting material is a whole seed flour or a flour from seeds partially freed of the outer skins or shells by sifting.

The delipidated flours partially freed of the seed shells contain between 37 and 44% by weight of proteins (N×6.25).

Various processes for obtaining and preparing extracts of *Hibiscus esculentus* or okra seeds will be described hereinafter by way of illustrative, non-limiting examples.

EXAMPLE 1

100 g of non-delipidated enriched flour (partially freed of the shell waste) in one liter of the following media:
  distilled water,
  distilled water containing 1 g/l of NaCl,
  distilled water containing 5 g/l of NaCl,
  distilled water containing 10 g/l of NaCl
are added.

After stirring for 15 minutes, the pH of the solution is adjusted to 9 with NaOH 4 N.

Extraction is carried out for one and a half hours at ambient temperature while keeping the pH at 9.

After centrifugation, the upper lipidic layer is removed and the aqueous supernatant liquid is collected.

The golden yellow supernatant liquid is adjusted to pH=7.5 then filtered to 0.22 µm; it is noted that the higher the salt content of the solvent, the easier filtration is.

The protein content of the filtrate is determined by the biuret method. The supernatant liquids remain opalescent.

The following results are obtained:

| Extraction solvent | Proteins in the biuret filtered extract (g/l) |
| --- | --- |
| distilled water | 16.9 |
| NaCl 1 g/l | 13.3 |
| NaCl 5 g/l | 9.5 |
| NaCl 10 g/l | 10.2 |

EXAMPLE 2

25 g of enriched delipidated flour (freed from shell debris) are added in 250 ml of distilled water containing 5 g/l of sodium chloride.

After stirring for 15 minutes, the pH of the solution is adjusted to the following pH according to the test: 6–6.5–7–7.5.

Extraction is carried out for one hour at ambient temperature.

After centrifugation, the supernatant liquid is recovered, then filtered over 5 µm.

The following results are obtained:

| pH | Biuret proteins (g/l) | Proteins (N × 6.25) (g/l) |
| --- | --- | --- |
| 6 | 12.5 | 13.8 |
| 6.5 | 13.3 | 14.8 |
| 7 | 14.6 | 15.1 |
| 7.5 | 15.5 | 16.1 |

EXAMPLE 3

25 g of enriched delipidated flour are added in 250 ml of distilled water containing 5 g/l of sodium chloride.

The pH of the solution is adjusted to 8 after stirring for 15 minutes.

Extraction is carried out for 6 hours at ambient temperature.

After centrifugation, the supernatant liquid is recovered and the pH adjusted to 7.5, then the solution is filtered over 5 µm.

The following results are obtained:

| Duration (hours) | Biuret proteins (g/l) |
| --- | --- |
| 2 | 18.45 |
| 4 | 20.3 |
| 6 | 19.7 |

EXAMPLE 4

25 g of enriched delipidated flour are added in 250 ml of distilled water containing 5 g/l of sodium chloride.

After stirring for 15 minutes, the pH of the solution is adjusted to pH 7.5.

Extraction is carried out for 6 hours at 45° C.

After centrifugation, the supernatant liquid is recovered, its pH is adjusted to 7.5 then the solution is filtered over 5 µm.

The following results are obtained:

| Duration (hours) | Biuret proteins (g/l) |
| --- | --- |
| 2 | 18.0 |
| 4 | 18.1 |
| 6 | 13.8 |

EXAMPLE 5

300 g enriched delipidated flour are added in 3 l of distilled water containing 5 g/l of sodium chloride.

After stirring for 15 minutes, the pH of the solution is adjusted to pH 7.5.

Extraction is carried out for 2 hours at 50° C.

After centrifugation, the supernatant is recovered then filtered over 5 μm.

The following results are obtained:

Biuret proteins: 13.7 g/l

Kjeldahl proteins: 14.6 g/l

One liter supernatant liquid is removed and its pH is adjusted to 4.5 using 4N sulphuric acid.

After 30 minutes of stirring, the solution is centrifuged and the precipitate is collected, then washed with water at pH 4.5. It is then freeze-dried: a powder of which the protein content is 85.3% by weight is obtained.

EXAMPLE 6

600 g of enriched delipidated flour in 6 liters of distilled water containing 5 g/l of NaCl are added while stirring in a thermostatically controller reactor. The pH measured is adjusted to 7.5.

The solution is pumped into an ultrasonic tube with an integral passage by means of a peristaltic pump (ultrasonic power 600 W—frequency 20,000 Hz), the flow rate being 60 l/h.

Two discontinuous passages by successive charges are produced (the extract is collected after passage in the ultrasonic tube in a second reactor).

After centrifugation, then filtration over 5 μm, the following results are obtained:

proteins from the extract after the first passage: 14.2 g/l proteins from the extract after the second passage: 15.2 g/l

EXAMPLE 7

300 g of enriched delipidated flour in 6 liters of distilled water containing 5 g/l of NaCl are added in a thermostatically controlled reactor while stirring. The measured pH is adjusted continuously to 7.5.

The solution is introduced continuously for 1 hour in a closed circuit in the integral passage ultrasonic tube from example 6 (ultrasonic power: 700 W—frequency: 20,000 Hz), the flow rate being 60 l/h.

A circulation of cold water allows the temperature of the solution in the vessel to be kept at about 33° C.

Samples are taken after 15 min, 30 min, and 45 min of extraction.

After centrifugation, then filtration of the extracts over 5 μm, the following results are obtained:

| Duration of extraction (min) | Proteins in the biuret filtered extract (g/l) |
| --- | --- |
| 15 | 8.23 |
| 30 | 8.56 |
| 45 | 8.89 |
| 60 | 9.89 |

EXAMPLE 8

25.0 kg of distilled water are introduced into a reactor and the following operations are carried out in succession:

dispersing with stirring 2.5 kg of whole flour obtained by crushing whole hibiscus seeds, adjusting the pH to 9 with NaOH 4N after 15 minutes of dispersion, extracting with stirring for 2 hours at ambient temperature while keeping the pH at 9 by addition of NaOH 4N, centrifuging for 10 minutes at 5,000 g, recovering the cloudy beige supernatant liquid, adjusting the pH to 7.5 by addition of H2SO4 4N, centrifuging, clarifying by renewed centrifugation, recovering the opalescent supernatant liquid, filtering to 0.5 μm, recovering the supernatant liquid, spraying.

A clear beige powder can therefore be recovered with a spray yield of 62.7% weight.

EXAMPLE 9

In a first variation of example 8, the following operations can also be carried out:

- adjusting the pH of a proportion of the extract prepared according to example 8 to 4.1 by addition of H2SO4 4N,
- leaving to rest at +4° C. (formation of a precipitate—about 50% of the total volume),
- centrifuging to 5,000 g for 15 min,
- washing the caps with distilled water at pH=4.1,
- centrifuging to 5,000 g for 15 min,
- collecting the precipitate,
- reconstituting the precipitate in distilled water (10% of the volume prior to precipitation),
- adjusting the pH to 7.5 by adding NaOH 4N while stirring,
- homogenising to assist solubilisation and homogenisation,
- centrifuging for 10 min at 5,000 g to eliminate the insoluble material,
- spraying the protein concentrate (spray yield based on the dry extract: 82.90% by weight).

EXAMPLE 10

In a second variation of example 8, the following operations can be carried out:

- adjusting the pH of a proportion of the extract prepared in example 8 to pH 5 by addition of H2SO4 4N,
- leaving to rest for one hour at ambient temperature,
- centrifuging,
- collecting the precipitate,
- reconstituting the precipitate in 10% of the volume prior to precipitation without carrying out the washing stage,
- adjusting the pH to 7.5 by adding NaOH 4N while stirring,
- homogenising to assist solubilisation and homogenisation,
- centrifuging for 10 min to 5,000 g to eliminate the insoluble material,
- atomising the protein concentrate.

BRIEF DESCRIPTION OF THE DRAWINGS

Gel permeation analysis over a column of the superose 12 HR type of the fraction extracted by the various methods described hereinbefore allows at least 6 different fractions to be characterised as shown in the diagrams in FIGS. 1 to 6 of the accompanying drawings, in which:

Figure 2:
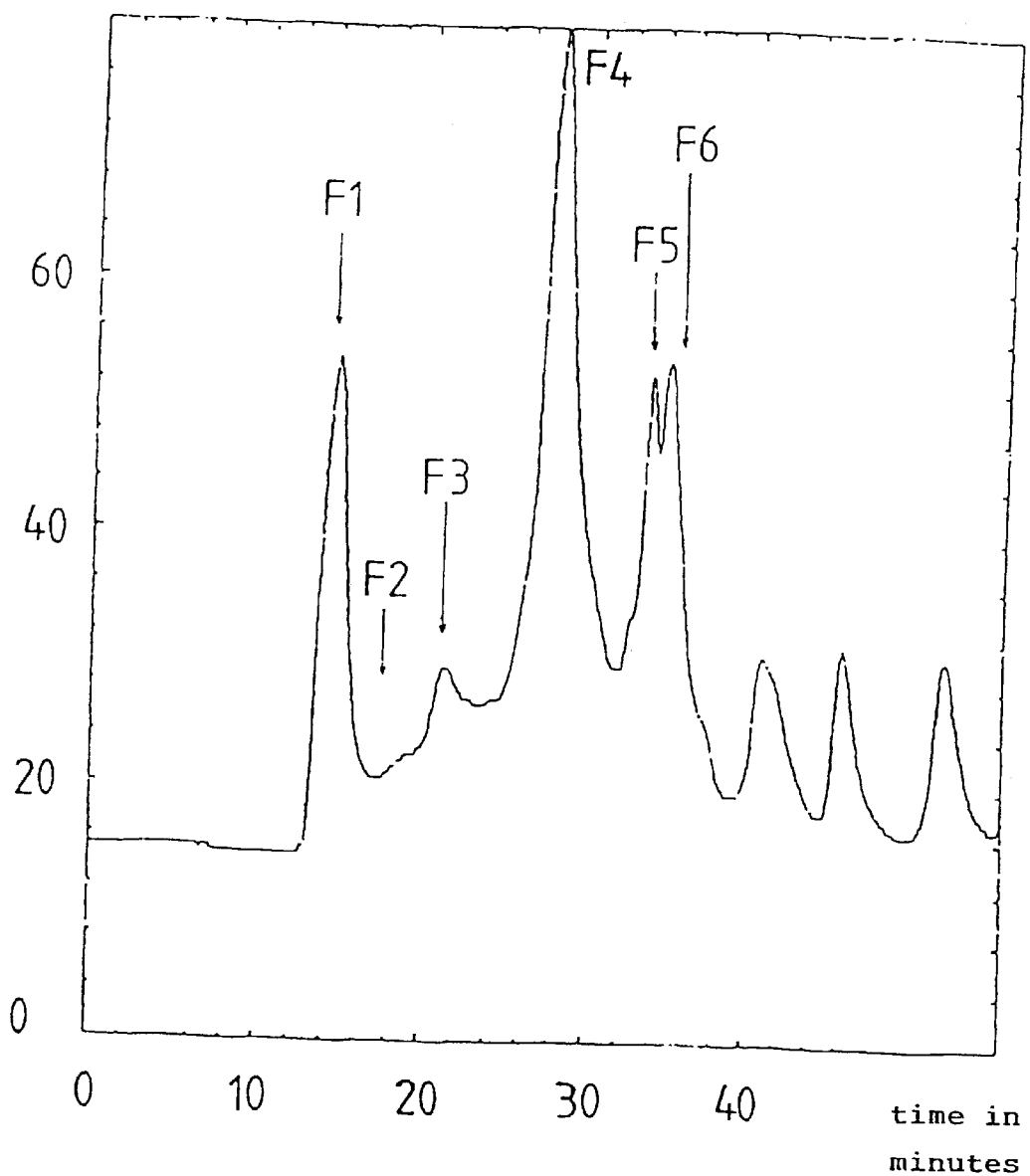
Figure 3:
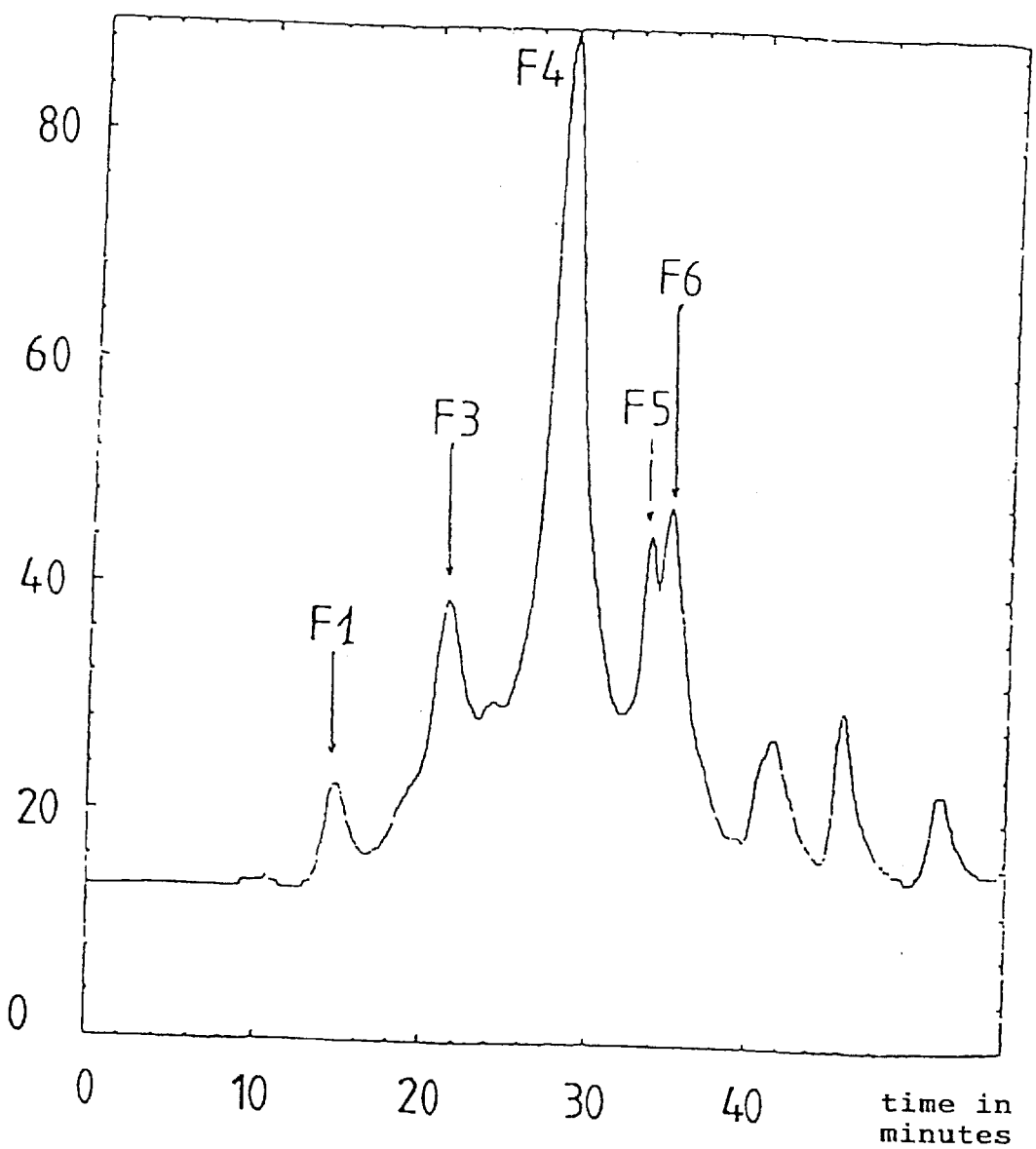
Figure 4:
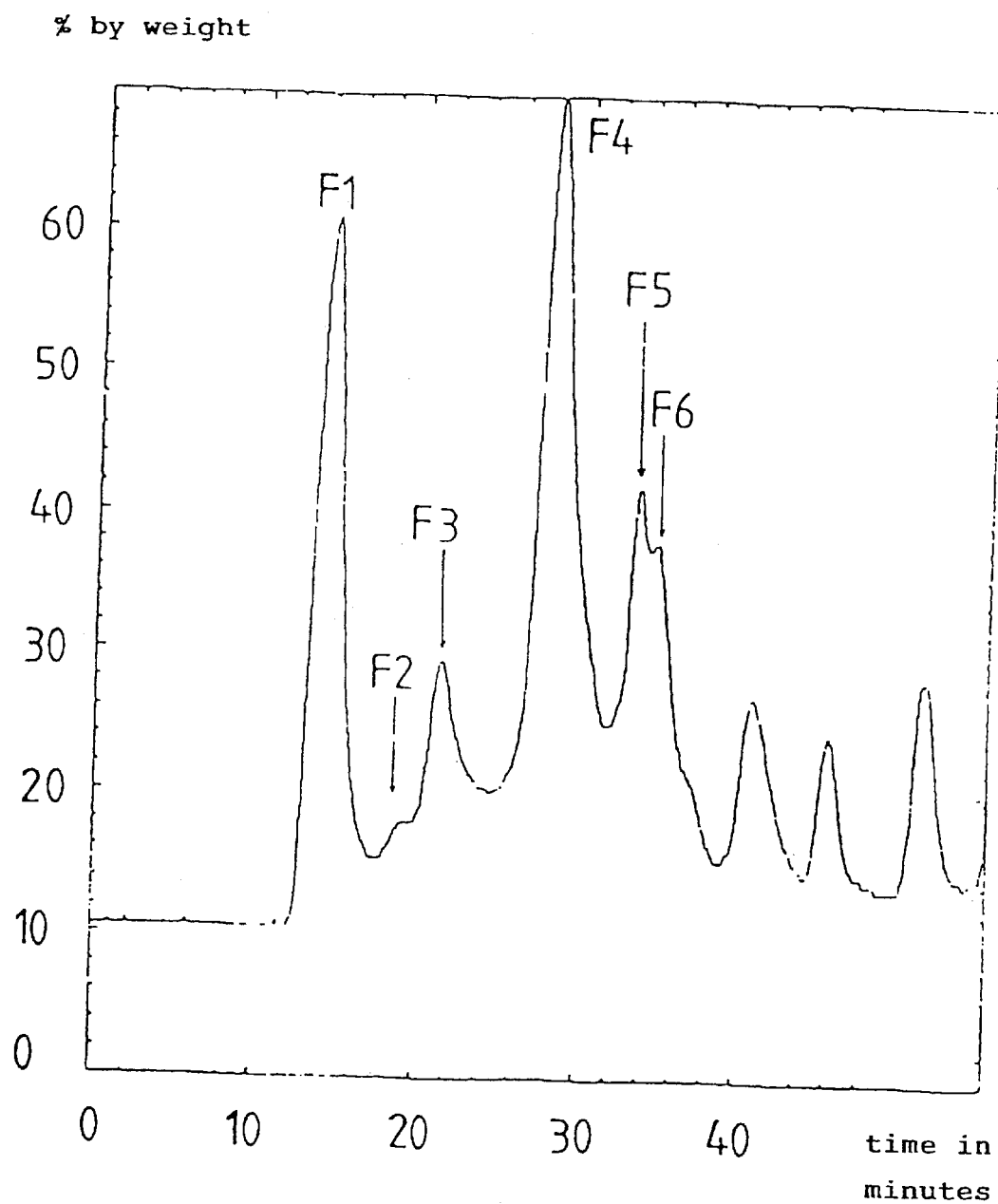
Figure 5:
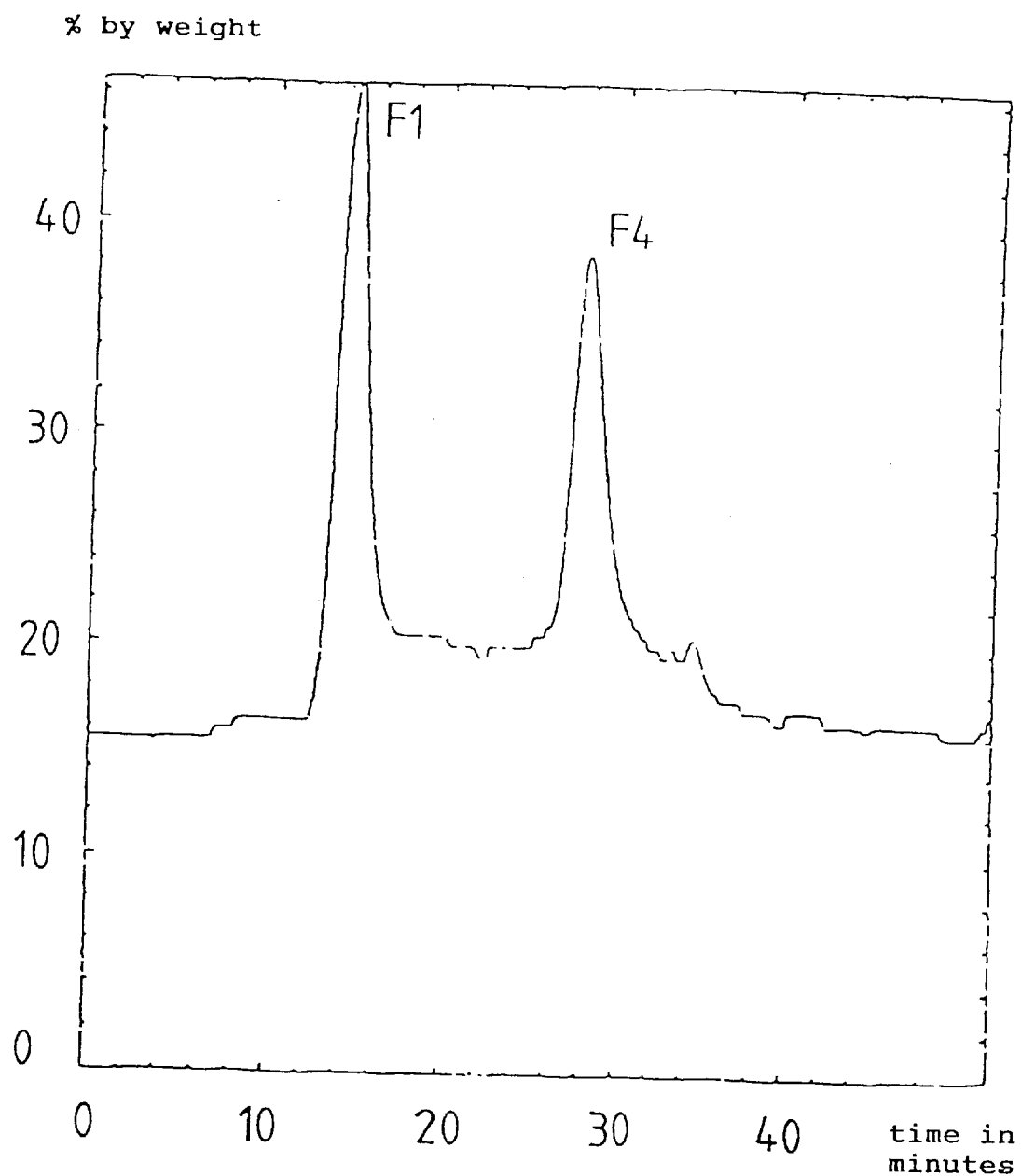
Figure 6:
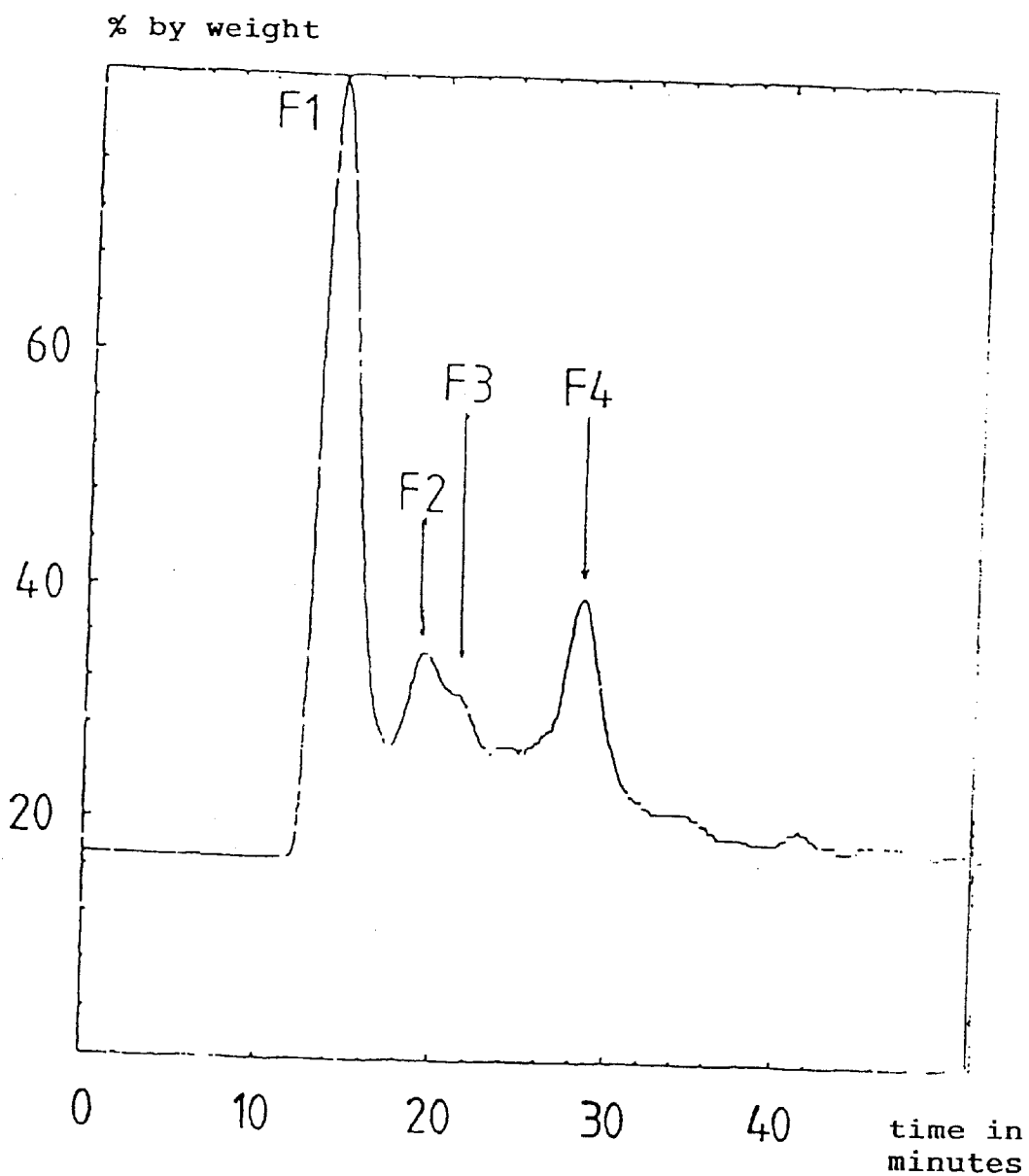

FIG. 1 shows the molecular weight distribution of the proteins of an extract of whole seed flour of *Hibiscus esculentus* (extraction: 2 hours at ambient temperature in water, pH=9), FIG. 2 shows the molecular weight distribution of the proteins of an extract of dehusked seed flour of *Hibiscus esculentus* (extraction: 1.5 hour at ambient temperature in water, pH=9), FIG. 3 shows the molecular weight distribution of the proteins of an extract of dehusked seed flour of *Hibiscus esculentus* (extraction: 1.5 hour at ambient temperature in NaCl 10 g/l, pH=9), FIG. 4 shows the molecular weight distribution of the proteins of an extract of dehusked seed flour of *Hibiscus esculentus* (extraction in an ultrasonic tube, 1 hour in NaCl 5 g/l, pH=7.5), FIG. 5 shows the molecular weight distribution of the proteins of a protein concentrate obtained by precipitation at pH=4.1 of an extract of whole seed flour of *Hibiscus esculentus*, and FIG. 6 shows the molecular weight distribution of the proteins of a protein concentrate obtained by precipitation at pH=5 of an extract of whole seed flour of *Hibiscus esculentus*.

DETAILED DESCRIPTION OF THE INVENTION

The following summary table (in two parts) shows the distribution of the various protein fractions extracted.

| Extraction conditions | pH = 9 water | pH = 9 NaCl 1 g/l | pH = 9 NaCl 5 g/l | pH = 9 NaCl 10 g/l | pH = 6.5 NaCl 5 g/l | pH = 8 NaCl 5 g/l 4h |
|---|---|---|---|---|---|---|
| PM > 500,000 Da | 13.7 | 9.8 | 4.4 | 3.7 | 2.9 | 2.7 |
| PM between 100,000 and 500,000 Da | 12.2 | 11.2 | 10.7 | 14.4 | 9.7 | 17.3 |
| PM between 30,000 and 100,000 Da | 4 | 3.3 | 7.6 | 7.7 | 14.7 | 7.9 |
| PM between 5,000 and 30,000 Da | 41.2 | 44.7 | 46.3 | 51.2 | 49.6 | 45.9 |
| PM lower than or equal to 5,000 Da | 28.9 | 31 | 31 | 23 | 23.1 | 26.2 |

| conditions | pH = 7.5 NaCl 5 g/l 6 h | pH = 7.5 NaCl 5 g/l 15 min US | pH = 7.5 NaCl 5 g/l 60 min US | pH = 9 H₂O whole flour | concentrate (pH 4.1) | Protein concentrate (pH 5) |
|---|---|---|---|---|---|---|
| PM > 500,000 Da | 4 | 13 | 20.9 | 30.5 | 35.5 | 46.6 |
| PM between 100,000 and 500,000 Da | 13.1 | 14.2 | 3.8 | 15 | 12.2 | 17.5 |
| PM between 30,000 and 100,000 Da | 4.3 | 6.1 | 15.1 | 5.9 | 8.1 | 7.3 |
| PM between 5,000 and 30,000 Da | 50.2 | 46 | 35.3 | 26.4 | 35.4 | 22.6 |
| PM lower than or equal to 5,000 Da | 28.4 | 20.7 | 24.9 | 22.2 | 8.8 | 6 |

The aforementioned 6 protein fractions consist of:

a fraction (designated F1) having a very high molecular weight (between 1,000,000 and 1,500,000 Da according to column calibration), a fraction (designated F2) having a molecular weight between 250,000 and 350,000 Da visible mainly on the extracts of whole seed flour, a fraction (designated F3) having a molecular weight between 130,000 and 180,000 Da, a fraction (designated F4) corresponding to a molecular weight between 17,000 and 22,000 Da, two molecular weight fractions of about 3,300 Da (F5) and about 2,300 to 2,600 Da (F6) respectively.

According to the extraction conditions, the fraction F1 constitutes between 2.7 and 50.00% of the proteins and the fraction F4 constitutes between 16 and 52% (average 40%) of the total proteins.

It is noted that, the higher the salt content of the extraction solvent at the outset, the smaller the fraction F1.

The extracts obtained by means of the examples of the described processes can be used directly in liquid form or after drying by conventional dehydration techniques (spraying, freeze-drying, etc.).

The protein fractions extracted according to the aforementioned examples have the advantage, relative to the natural state in which they occur in the seeds, of having an identical native chemical structure, of being able to be partially or completely purified (that is freed of other seed components such as lipids, fibres, saccharoses or the like) and of having a composition which can be varied as a function of the extraction and/or purification process employed (total proteins of the crude extract, protein concentrate or purified protein fraction(s).

In relation to lactic casein, improved solubility is noted in addition to the desired renewable vegetable origin in the cosmetics field, while maintaining an amino acid composition close to casein, of which the nutritional, moisturising and film-forming properties for skin and the superficial body growths are known.

The protein fractions can be used either in their native form without modification of the initial structures or in the form of natural associations of two or of all the extracted fractions corresponding to the various peaks of the chromatograms shown in the accompanying drawings or again in isolated form, that is the use of one or more fractions corresponding to one or more peaks of the aforementioned chromatograms.

The protein fractions can also be used in the form modified or functionalised by any one of the following treatments:

polymerisation, chemical hydrolysis of the hibiscus proteins enzymatic hydrolysis of the hibiscus proteins. To this end, proteases originating from extracts of animal, vegetable, microbial or fungal origin can be used to modify the hibiscus proteins: pepsin, trypsin, chymotrypsin/papain, pronase, bromelain/endoproteinase, thermitase, proteases of *Bacillus subtilis, Aspergillus Niger* and *Aspergillus Oryzae/subtilisine, alcalase, neutrase*.

microbiological transformation with use of hibiscus proteins as substrate for fermentation by various microorganisms such as yeasts (Saccharomyces), mould fungus (of the Aspergillus type), bacteria such as Bacillus or the like.

chemical or enzymatic functionalisation by processes such as desamidation, succinylation or phosphorylation.

quaternisation.

grafting of saccharidic or lipidic molecules.

The invention also relates to a cosmetic composition, in particular for topical application, for the skin and/or the superficial body growths, characterised in that it contains at least one preferably soluble protein fraction extracted from *Hibiscus esculentus* seeds as substitute for casein.

According to a characteristic of the invention, the protein fraction(s) is (are) extracted from non-delipidated or delipidated flour of whole or dehusked *Hibiscus esculentus* seeds by water or saline solutions at various pH.

According to a preferred embodiment of the invention, the protein fraction(s) is (are) extracted in aqueous solution under the influence of ultrasound and this fraction(s) is (are) purified by a purification process selected from the group formed by precipitation, absorption, ion or affinity exchange chromatography and ultrafiltration.

The total or native protein fraction is selected from the group of total and native protein fractions extracted from *Hibiscus esculentus* seeds and having apparent molecular weights when filtered over gel of 1,000,000 to 1,500,000 Da, 250,000 to 350,000 Da, 130,000 to 180,000 Da, 17,000 to 22,000 Da, 3,300 Da and 2,300 to 2,600 Da.

The aforementioned protein fraction(s) can consist of a chemical or enzymatic hydrolysate prepared from native proteins, can be obtained by polymerisation or depolymerisation of native proteins or can be chemically modified by grafting.

According to a first embodiment of the invention, the cosmetic composition contains at least two protein fractions of different apparent molecular weights.

According to a second embodiment of the invention, the cosmetic composition contains an extract of *Hibiscus esculentus* seeds consisting of all the soluble protein fractions naturally present in these seeds.

The cosmetic composition of the present invention is characterised in that it preferably contains between 0.01% and 50.00% by weight, preferably between 1 and 25% by weight, of protein fraction(s) extracted from *Hibiscus esculentus* seeds as obtained in any one of the examples of processes described hereinbefore.

As non-limiting embodiments of the invention, various cosmetic products or compositions containing at least one soluble protein fraction extracted from *Hibiscus esculentus* or okra seeds will be described hereinafter.

EXAMPLE 1

A cosmetic product according to the invention, in the form of a moisturising smoothing day cream for the face and body can, for example, have a composition by weight made up of the following fractions A, B, C and D, as indicated hereinafter.

| Fraction A: | |
| --- | --- |
| Cutina MD | 14.00% |
| Eutanol G | 6.00% |
| Cetiol B | 6.00% |
| Eumulgin B1 | 1.50% |
| Eumulgin B2 | 1.50% |
| Fraction B: | |
| Extracts of total native proteins from hibiscus according to the aforementioned example 1 | 8.00% |
| Fraction C: | |
| Allantoin | 0.20% |
| Methylparaben | 0.20% |
| Germall 115 | 0.30% |
| Distilled water | 62.00% |
| Fraction D: | |
| Fragrance | 0.30% |

The process for the preparation and production of the aforementioned day cream essentially involves heating fraction A to 75° C., preparing fraction C at 75° C., pouring fraction A into fraction B with turbine stirring, adding fraction C at about 50° C. then continuing planetary stirring to ambient temperature and finally adding fraction D.

EXAMPLE 2

A cosmetic product according to the invention in the form of a restructuring, anti-wrinkle nourishing repairing night cream could, for example, have a composition by weight consisting of the following fractions A, B, C and D, as mentioned hereinafter.

| Fraction A: | |
| --- | --- |
| Miglyol 810 | 6.00% |
| Myrj 51 | 3.00% |
| Arlatone 983 S | 2.00% |
| Stearic acid TP | 4.00% |
| Cetyl alcohol | 3.00% |
| Fraction B: | |
| Propylene glycol | 3.00% |
| Elestab LS 388 (Laboratoires Serobiologiques) | 2.50% |
| Distilled water | 61.20% |
| Fraction C: | |
| Sprayed extracts of native hibiscus proteins according to the aforementioned example 9 | 2.00% |
| Distilled water | 13.00% |
| Fraction D: | |
| Fragrance | 0.30% |

The process for preparing and producing the aforementioned night cream essentially involves preparing and heating fractions A and B to 75° C., pouring fraction A into fraction B with turbine stirring, preparing (separately and extemporaneously) the solute of fraction C by stirring of the atomisate in distilled waters adding fraction C to emulsion A+B while cooling to about 50° C., then continuing planetary stirring from 45° C. and to ambient temperature while adding the fragrance at about 40° C.

EXAMPLE 3

A cosmetic product according to the invention in the form of a protective conditioning covering light-protective microemulsion for hair could, for example, have a composition by weight made up of the following fractions A, B, C and D, as mentioned hereinafter.

| Fraction A: | |
| --- | --- |
| Brij 96 | 11.80% |
| Arlatone G | 10.00% |
| Paraffin oil | 13.00% |

-continued

| Fraction B: | |
|---|---|
| Distilled water | 53.70% |
| Methylparaben | 0.20% |
| Elestab 4112 | 0.30% |
| (Laboratoires Serobiologiques) | |
| Fraction C: | |
| Native hibiscus proteins in the form of a protein concentrate according to the aforementioned example 6 | 5.00% |
| Distilled water | 5.00% |
| Fraction D: | |
| Fragrance | 0.20% |
| Tween 20 | 0.80% |

The process for preparing and producing the aforementioned microemulsion essentially involves preparing and heating fraction A and B to 75° C., pouring fraction A into fraction B with turbine stirring, carrying out progressive cooling and, at about 50° C., adding the fraction C then the fraction D and continuing stirring until cooling to ambient temperature and perfect homogenisation.

The invention is obviously not limited to the embodiments described and illustrated in the accompanying drawings. Modifications are possible, in particular with regard to the composition of the various elements or by substitution of technical equivalents, without departing from the scope of protection of the invention.

What is claimed is:

1. A cosmetic composition, which comprises at least one emulsifier, a fragrance, a cosmetically acceptable carrier, and protein-containing fractions extracted from *Hibiscus esculentus* seeds as a substitute for casein, said protein-containing fractions being extracted from non-delipidated or delipidated flour of whole or dehusked *Hibiscus esculentus* seeds by water or saline solutions at a pH between 4.1 and 9, wherein at least some of said protein-containing fractions extracted from *Hibiscus esculentus* seeds have apparent molecular weights when filtered over gel in the ranges of 1,000,000 to 1,500,000 Da, and 17,000 to 22,200 Da, wherein 2.7 to 50% of said protein-containing fractions are in the 1,000,000 to 1,500,000 Da range and 16–52% of said protein-containing fractions are in the 17,000 to 22,000 Da range, and said composition contains between 0.05% to 50% by weight of said protein-containing fractions.

2. The cosmetic composition according to claim 1, wherein the protein fraction having an apparent molecular weight between 17,000 to 22,000 Da is present in an amount between 16 and 52% of the total proteins.

3. The cosmetic composition according to claim 1, further comprising protein-containing fractions extracted from *Hibiscus esculentus* seeds that have apparent molecular weights when filtered over gel in the ranges of 250,000 to 350,000 Da; 130,000 to 180,000 Da; 3,300 Da; and 2,300 to 2,600 Da.

4. A cosmetic composition, which comprises:
   at least one emulsifier;
   a fragrance;
   a cosmetically acceptable carrier; and
   at least two protein-containing fractions extracted from *Hibiscus esculentus* seeds as a substitute for casein, said protein fractions being extracted from non-delipidated or delipidated flour of whole or dehusked *Hibiscus esculentus* seeds by water or saline solutions at a pH between 4.1 and 9, wherein said protein fractions-containing extracted from *Hibiscus esculentus* seeds have apparent molecular weights when filtered over gel in the ranges of 1,000,000 to 1,500,000 Da, and 17,000 to 22,200 Da, wherein 2.7 to 50% of said protein-containing fractions are in the 1,000,000 to 1,500,000 Da range and 16–52% of said protein-containing fractions are in the 17,000 to 22,000 Da range, and said composition contains between 1% to 25% by weight of protein-containing fractions extracted from *Hibiscus esculentus* seeds.

5. The cosmetic composition according to claim 4, further comprising protein-containing fractions extracted from *Hibiscus esculentus* seeds that have apparent molecular weights when filtered over gel in the ranges of 250,000 to 350,000 Da; 130,000 to 180,000 Da; 3,300 Da; and 2,300 to 2,600 Da.

* * * * *

UNITED STATES PATENT AND TRADEMARK OFFICE
CERTIFICATE OF CORRECTION

PATENT NO. : 6,379,719 B1
DATED : April 30, 2002
INVENTOR(S) : Gilles Pauly

It is certified that error appears in the above-identified patent and that said Letters Patent is hereby corrected as shown below:

<u>Title page,</u>
Amend Item [12], to read as follows: -- [12] Pauly --.
Amend Item [75], to read as follows: -- [75] Gilles Pauly, Nancy (FR) --.

Signed and Sealed this

Thirtieth Day of July, 2002

*Attest:*

*Attesting Officer*

JAMES E. ROGAN
*Director of the United States Patent and Trademark Office*